US012714529B2

(12) United States Patent
Annen et al.

(10) Patent No.: US 12,714,529 B2
(45) Date of Patent: Aug. 25, 2026

(54) METHOD AND APPARATUS FOR PROVIDING STERILE COVER FOR NON-CONTACT FUNDUS VIEWING DEVICE

(71) Applicant: OCULUS Optikgeräte GmbH, Wetzlar (DE)

(72) Inventors: Michael Annen, Ft. Pierce, FL (US); William O'Brien, Port St. Lucie, FL (US); Steffen Adamowicz, Solms (DE)

(73) Assignee: OCULUS OPTIKGERATE GMBH, Wetzlar (DE)

( * ) Notice: Subject to any disclaimer, the term of this patent is extended or adjusted under 35 U.S.C. 154(b) by 1141 days.

(21) Appl. No.: 17/776,504

(22) PCT Filed: Nov. 12, 2020

(86) PCT No.: PCT/IB2020/001017
§ 371 (c)(1),
(2) Date: May 12, 2022

(87) PCT Pub. No.: WO2021/094835
PCT Pub. Date: May 20, 2021

(65) Prior Publication Data

US 2022/0378540 A1 Dec. 1, 2022

Related U.S. Application Data

(60) Provisional application No. 62/934,262, filed on Nov. 12, 2019.

(51) Int. Cl.
*A61B 46/10* (2016.01)
*A61B 46/00* (2016.01)
(Continued)

(52) U.S. Cl.
CPC .............. *A61B 46/10* (2016.02); *A61B 46/40* (2016.02); *G02B 23/16* (2013.01);
(Continued)

(58) Field of Classification Search
None
See application file for complete search history.

(56) References Cited

U.S. PATENT DOCUMENTS 6,318,864 B1 * 11/2001 Fukaya .................. A61B 46/10 359/368
2004/0190139 A1 9/2004 Weaver et al.
(Continued)

FOREIGN PATENT DOCUMENTS

JP 2016007234 A 1/2016

OTHER PUBLICATIONS

IN 23224532678, India Examination Report, Mailed Jan. 13, 2023, 6 pages.
(Continued)

*Primary Examiner* — Dung T Nguyen
(74) *Attorney, Agent, or Firm* — Timothy H. Van Dyke; Wolter, Van Dyke, Davis, PLLC

(57) ABSTRACT

An apparatus is provided including a sterile cover. The sterile cover includes a first portion (202) that defines a first cavity such that the first portion is configured to secure a non-sterile inverter (106) of a wide angle viewing attachment for a microscope within the first cavity. The sterile cover also includes a second portion integral with the first portion. The second portion defines a second cavity continuous with the first cavity. The second portion is configured to secure an imaging lens (201) of the microscope within the second cavity. A method is provided for using the microscope including the apparatus. A method is provided for forming the apparatus.

25 Claims, 14 Drawing Sheets

(51) Int. Cl.

| | |
|---|---|
| ***G02B 23/16*** | (2006.01) |
| ***G02B 23/24*** | (2006.01) |
| *A61B 3/13* | (2006.01) |
| *A61B 90/00* | (2016.01) |
| *A61B 90/20* | (2016.01) |
| *B29C 39/02* | (2006.01) |
| *B29L 31/00* | (2006.01) |
| *B33Y 80/00* | (2015.01) |

(52) U.S. Cl.
CPC ............ *G02B 23/2476* (2013.01); *A61B 3/13* (2013.01); *A61B 2090/0814* (2016.02); *A61B 90/20* (2016.02); *B29C 39/02* (2013.01); *B29L 2031/7546* (2013.01); *B33Y 80/00* (2014.12)

(56) References Cited

U.S. PATENT DOCUMENTS

| | | | |
|---|---|---|---|
| 2007/0064309 | A1 | 3/2007 | Luloh et al. |
| 2011/0235168 | A1 | 9/2011 | Sander |
| 2017/0184842 | A1 | 6/2017 | Shen et al. |
| 2018/0280101 | A1 | 10/2018 | Ueda |

OTHER PUBLICATIONS

PCT Search report & written opinion, PCT/IB2020/001017, mailed Apr. 6, 2021, 48 pages.
CN 202080093170.2, Office Action mailed Sep. 23, 2024, 12 pages.

* cited by examiner

METHOD AND APPARATUS FOR PROVIDING STERILE COVER FOR NON-CONTACT FUNDUS VIEWING DEVICE

CROSS-REFERENCE TO RELATED APPLICATIONS

This application claims benefit of U.S. Provisional Application No. 62/934,262, filed Nov. 12, 2019, the entire contents of which is hereby incorporated by reference as if fully set forth herein, under 35 U.S.C. § 119(e).

BACKGROUND

FIG. 1A is an image that illustrates an example of a perspective view of a conventional ophthalmic operating microscope system with a wide-angle viewing attachment that includes a non-sterile inverter 106 and imaging lens housing 104 removably attached to the non-sterile inverter 106, in addition to their associated fixturing. A conventional ophthalmic operating microscope is used by surgeons and assistants for improved visualization during many surgical procedures involving the eye and orbital structures. The conventional opthalmic operating microscope is typically a stereoscopic microscope with a working distance in a range from about 175 mm to about 225 mm, and a magnification range from about 5× to about 25×. In specific procedures involving the retina, ocular fundus, and areas of the vitreos humor, an additional set of optics is generally used to view these structures through the limited aperture of the pupil. The optic that makes it possible to view the posterior structures through the pupil is a wide-angle lens which must be positioned very close to the eye and is characterized by having a very high diopter. When the additional optics are supported by and attached to the microscope it can be referred to as a wide-angle viewing attachment. The combination of the viewing attachment and the operating microscope together can be referred to as a conventional posterior ophthalmic operating microscope system. One example of such a conventional posterior ophthalmic operating microscope system 100 is the Haag-Streit Erect Indirect Binocular Ophthalmic System (EIBOS®) (originally developed by Moeller-Wedel, a division of the Haag-Streit Group). The imaging lens housing 104 (with lens) is positioned proximal to the eye of the surgical patient and creates an inverted virtual image of the fundus. The non-sterile inverter 106, typically consisting of a series of prisms, mirrors and lenses, is used to reinvert the image to an orientation representative of the surgical field, which is viewed through the oculars 102. This non-sterile inverter 106 may be positioned between the microscope 100 body and the oculars 102, or in the case of the system 100 (FIG. 1A) is integrated into the viewing attachment between the imaging lens housing 104 and the microscope objective 105.

SUMMARY

Due to the delicate opto-mechanical construction of the conventional microscope system 100, the non-sterile inverter 106 cannot be sterilized in a practical manner (e.g. with steam autoclave). Thus, conventional sterile covers have been developed (e.g. silicone cover 120 in FIG. 1B) to separate the sterile surgical field from the non-sterile inverter 106 and microscope system 100. FIG. 1C depicts the non-sterile inverter 106 secured within the silicone cover 120 and with the imaging lens housing 104 secured outside the silicone cover 120. After performing surgery using the conventional microscope system 100, the inventors of the present invention recognized that the system 100 requires disassembly prior to sterilization. Such disassembly involves several steps including removal of knobs 112, detaching the imaging lens housing 104 from the non-sterile inverter 106, removing the non-sterile inverter 106 from the silicone cover 120 and subsequently sterilizing (e.g. steam autoclave) the knob 112, imaging lens housing 104 and silicone cover 120 before reassembling the system 100. Additionally, although some conventional systems offer a disposable imaging lens and housing 104, the inventors noticed that sterilization would still require disassembling and sterilization of the knobs 112 and silicone cover 120 before reassembling the microscope system. The inventors of the present invention realized that these conventional systems involve reprocessing time that is costly, the component of the systems are susceptible to degradation such as coating failure and mineral deposits on the optical surface, while the silicone cover 120 can wear out due to repeated use and high/low temperature cycles.

In order to overcome the above noted drawbacks of conventional microscope systems and conventional silicone covers, the inventors of the present invention developed the sterile cover discussed herein. In one embodiment, the inventors of the present invention recognized that a disposable sterile cover could be designed which integrated the imaging lens housing, so that the non-sterile inverter 106 and a disposable imaging lens could be secured within the disposable sterile cover. In an embodiment, the disposable imaging lens is sterile. After performing eye surgery, the sterile cover, knobs and imaging lens could then be conveniently disposed and no disassembly and sterilization of the microscope system components would be required. Instead, the sterile cover and imaging lens would just need to be replaced with another sterile cover and imaging lens. The inventors of the present invention even developed a design feature to ensure that each sterile cover is used only once, to prevent reuse. The inventors of the present invention also recognized that the sterile cover could include integrated knobs so that separate knobs would not need to be detached and sterilized.

In a first embodiment, an apparatus is provided including a sterile cover. The sterile cover includes a first portion that defines a first cavity such that the first portion is configured to secure a non-sterile inverter of a microscope within the first cavity. The sterile cover also includes a second portion integral with the first portion. The second portion defines a second cavity continuous with the first cavity. The second portion is configured to secure an imaging lens of the microscope within the second cavity.

In a second embodiment, a method is provided for using the microscope including an apparatus. The method includes securing a first sterile cover of the apparatus over the non-sterile inverter of the microscope such that the non-sterile inverter is secured in a first portion of the first sterile cover and the imaging lens is in a second portion of the first sterile cover. The non-sterile inverter and imaging lens are aligned along an optical axis. The method further includes performing eye surgery using the non-sterile inverter and the imaging lens within the first sterile cover. The method further includes removing and/or destruction (for prevention of reuse) of the first sterile cover from the non-sterile inverter of the microscope. The method further includes disposing the first sterile cover and the imaging lens secured in the second portion of the first sterile cover. The method further includes securing a second sterile cover over the non-sterile inverter of the microscope such that the non-sterile inverter is secured in the first portion of the second sterile cover and the imaging lens is secured in the second portion of the second sterile cover such that the non-sterile inverter and imaging lens are aligned along an optical axis.

In a third embodiment, a molding or casting method is provided for forming an apparatus. The method includes providing a mold with a cavity defined by the sterile cover of the apparatus. The method further includes providing a liquid material into the mold. The method further includes curing the liquid material into a solid material. The method further includes removing the solid material defining the sterile cover from the mold.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus are described for providing a sterile cover for a non-contact fundus viewing device. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term “about” is used to indicate a broader range centered on the given value, and unless otherwise clear from the context implies a broader range around the least significant digit, such as “about 1.1” implies a range from 1.0 to 1.2. If the least significant digit is unclear, then the term “about” implies a factor of two, e.g., “about X” implies a value in the range from 0.5× to 2×, for example, about 100 implies a value in a range from 50 to 200. Moreover, all ranges disclosed herein are to be understood to encompass any and all sub-ranges subsumed therein. For example, a range of “less than 10” for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of sterile covers for viewing devices, specifically microscopes. However, the invention is not limited to this context. In other embodiments, the invention can be employed in the context of handheld sterile observation instruments/tools, e.g. a cover for a microscope or any other attachments for the microscope.

For purposes of this description, the term “cover” means an element or component that is used to provide a sterile barrier between a sterile surgical field being viewed by a viewing device and one or more non-sterile components of the viewing device (e.g. non-sterile inverter 106).

Figures 2A, 2B:
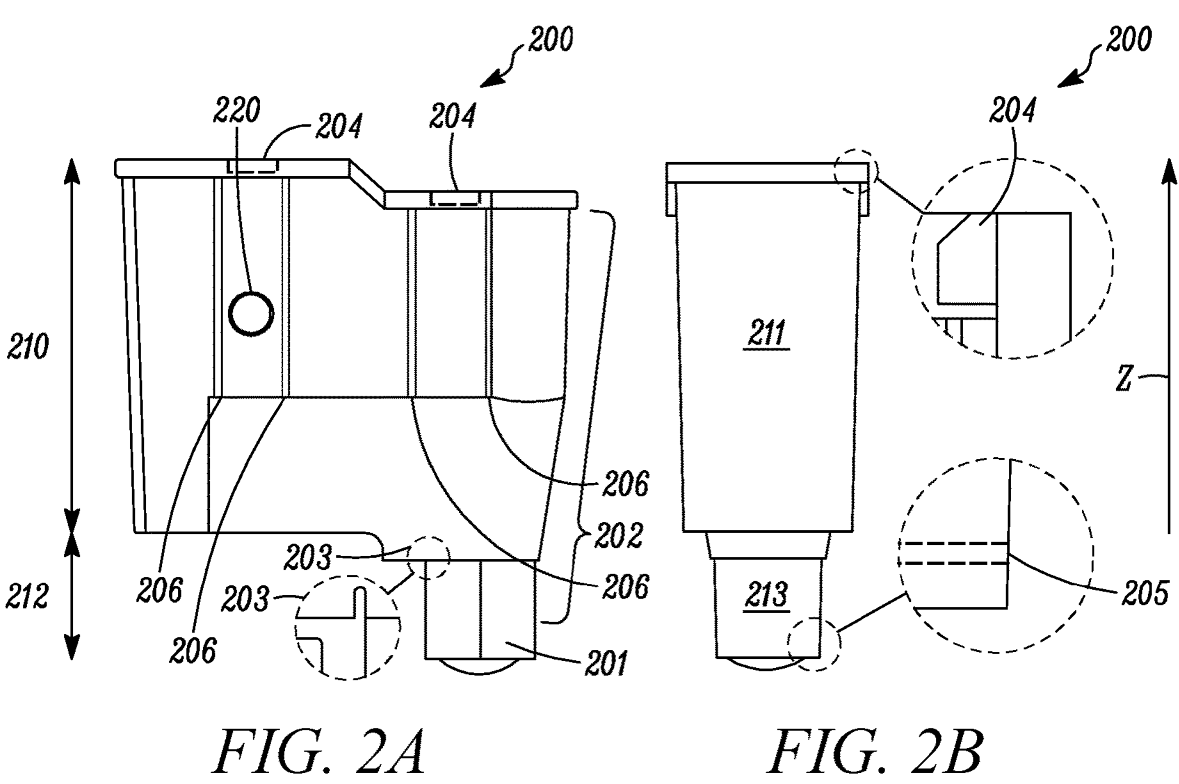
FIGS. 2A-2C are schematic diagrams that illustrate example views of a sterile cover, according to an embodiment.
Figure 2C:
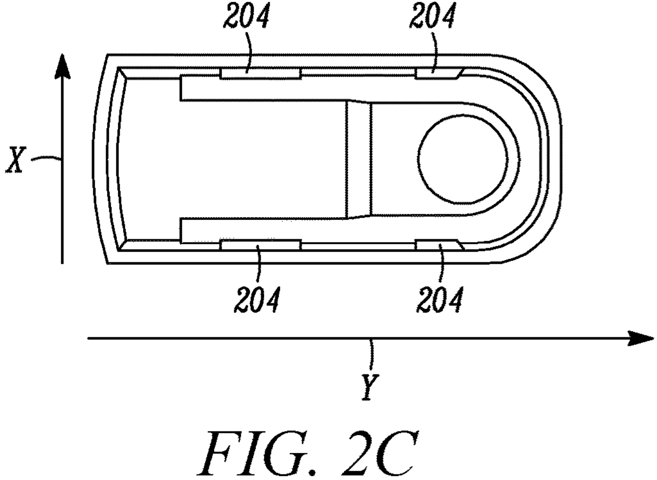

FIGS. 2A-2C are schematic diagrams that illustrate example views of an apparatus 200 including a sterile cover 202, according to an embodiment. In an embodiment, the sterile cover 202 includes a first portion 210 that is configured to secure the non-sterile inverter 106 within a first cavity 211 defined by the first portion 210. Additionally, in an embodiment, the sterile cover 202 includes a second portion 212 that is configured to secure an imaging lens 201 of the microscope within a second cavity 213 defined by the second portion 212. In an embodiment, the first cavity 211 is continuous with the second cavity 213. For purposes of this description, "continuous" means that the first cavity 211 and the second cavity 213 form one collective cavity of the sterile cover 202 and/or there is no boundary between the first cavity 211 and the second cavity 213. In an example embodiment, the first cavity 211 has a larger volume than the second cavity 213. In still other embodiments, the first portion 210 and first cavity 211 take a rectangular and/or an elongated oval shape whereas the second portion 212 and second cavity 213 take a cylindrical and/or conical section shape. In an example embodiment, the first cavity 211 has a height of about 70 millimeters (mm) or in a range from about 55 mm to about 85 mm (e.g. where the height is measured along the Z axis depicted in FIGS. 2A-2B). In another example embodiment, the first cavity 211 has a width of about 40 mm or in a range from about 30 mm to about 50 mm (e.g. where the width is measured along the X axis depicted in FIG. 2C). In another example embodiment, the first cavity 211 has a depth of about 80 mm or in a range from about 65 mm to about 95 mm (e.g. where the depth is measured along the Y axis depicted in FIG. 2C). In another example embodiment, the second cavity 213 has a height of about 20 mm or in a range from about 5 mm to about 25 mm, a width of about 20 mm or in a range from about 15 mm to about 25 mm and a depth of about 20 mm or in a range from about 15 mm to about 25 mm. In one example embodiment, the second cavity 213 is a cylindrical cavity or a conical section cavity. In an example embodiment, the height, width and/or depth of the second cavity 213 are measured along similar X, Y, Z axes (FIGS. 2A-2C) as the first cavity 211.

In an embodiment, the sterile cover 202 is made from a semi-rigid material. For purposes of this description, "semi-rigid material" means a material with a value of a parameter within one or more ranges. In one embodiment, the parameter is flexural modulus and the value of the parameter is greater than 100 Megapascal (MPa) and/or in a range between about 100 MPa and about 1500 Mpa and/or in a range between about 130 MPa and about 1400 MPa. In yet another embodiment, the parameter is flexural strength and the value of the parameter is about 40 MPa and/or in a range from about 10 MPa to about 100 MPa. In another embodiment, the sterile cover 202 is made from a semi-rigid molded plastic material. In still another embodiment, the sterile cover 202 is made from a disposable material and/or a sterilizable material. For purposes of this description, "sterilizable material" is a material which maintains its functional properties (e.g. semi-rigid material properties, tear strip properties, etc.) after sterilizing said material. In yet another embodiment, the lens 201 is also made from the sterilizable material. In an example embodiment, the material used to form the sterile cover 202 and/or the lens 201 and/or the semi-rigid material and/or the sterilizable material includes one or more of Polypropylene (PP), High-density polyethylene (HDPE), Low-density polyethylene (LDPE), Polyethylene (PE), Polyethylene terephthalate (PET), medical-grade Silicone/Rubbers, sterilizable material, recyclable material, non-allergenic material and/or bio-compatible material.

Figure 1A:
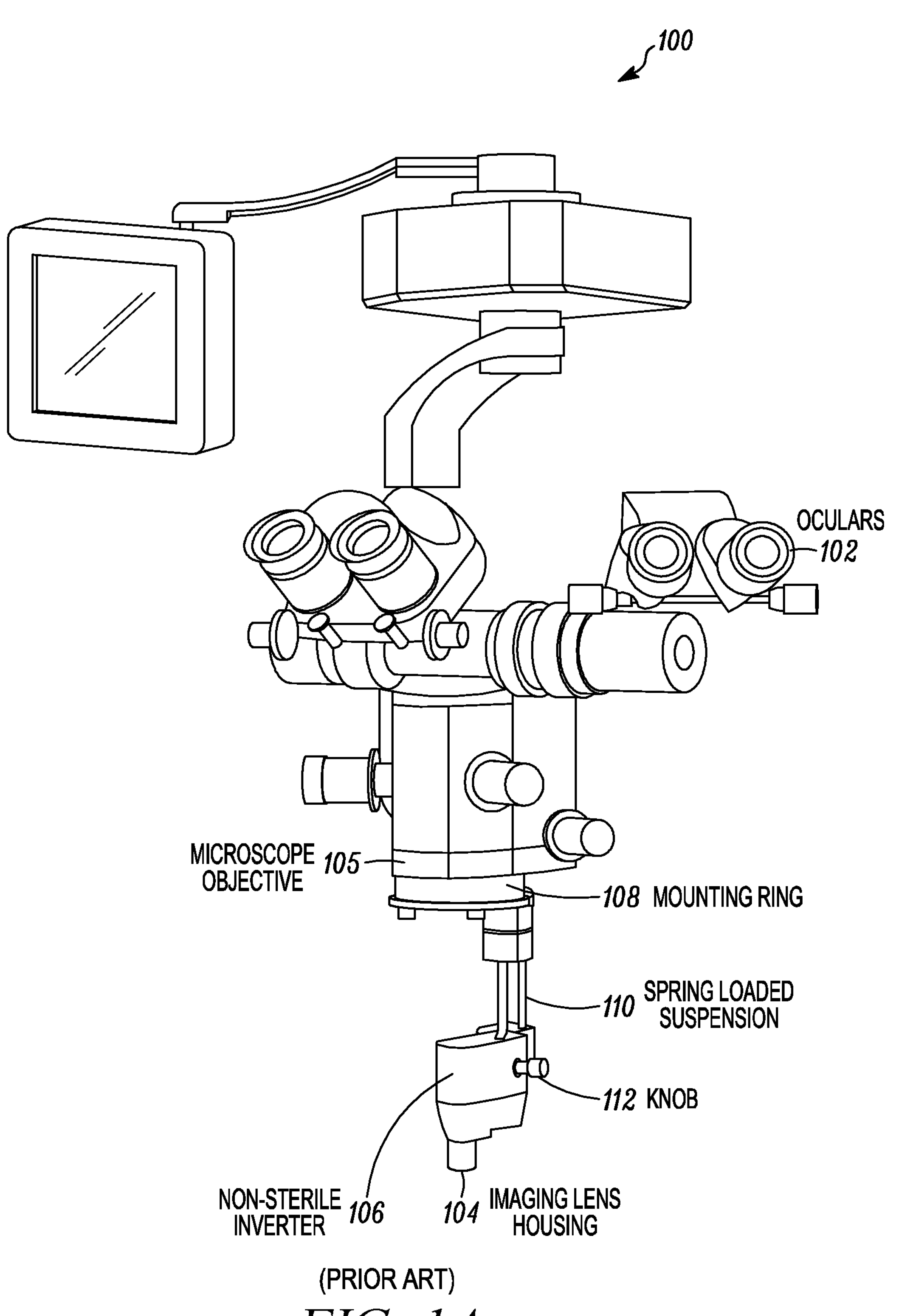
FIG. 1A is an image that illustrates an example of a perspective view of a conventional ophthalmic operating microscope including a non-sterile inverter and imaging lens housing.
Figure 1B:
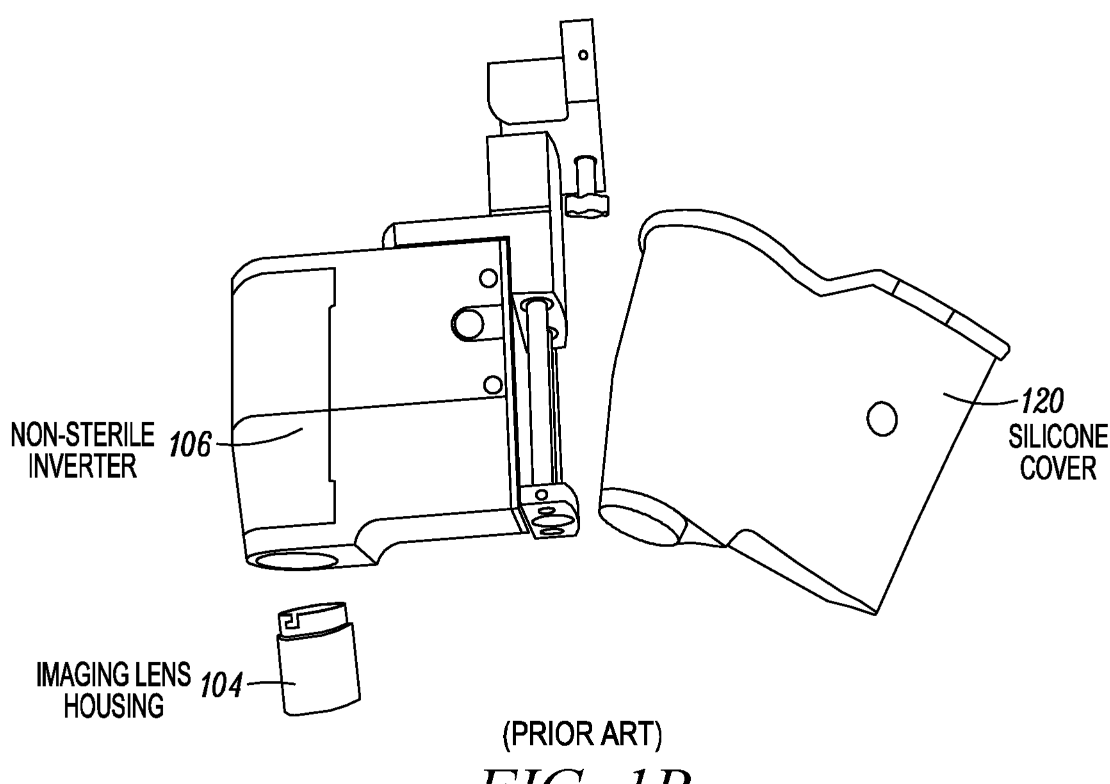
FIG. 1B is an image that illustrates an example of a side view of the conventional imaging lens housing and non-sterile inverter of FIG. 1A and a conventional silicone cover.
Figure 1C:
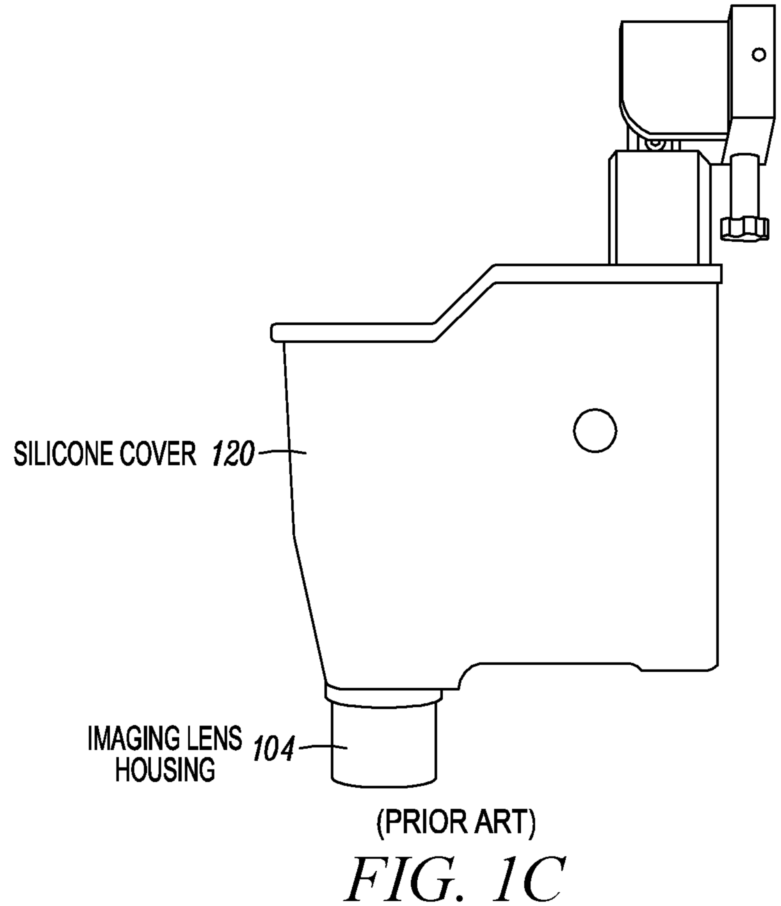
FIG. 1C is an image that illustrates an example of a side view of the non-sterile inverter of FIG. 1A secured within the conventional silicone cover of FIG. 1B.
Figures 3A, 3B:
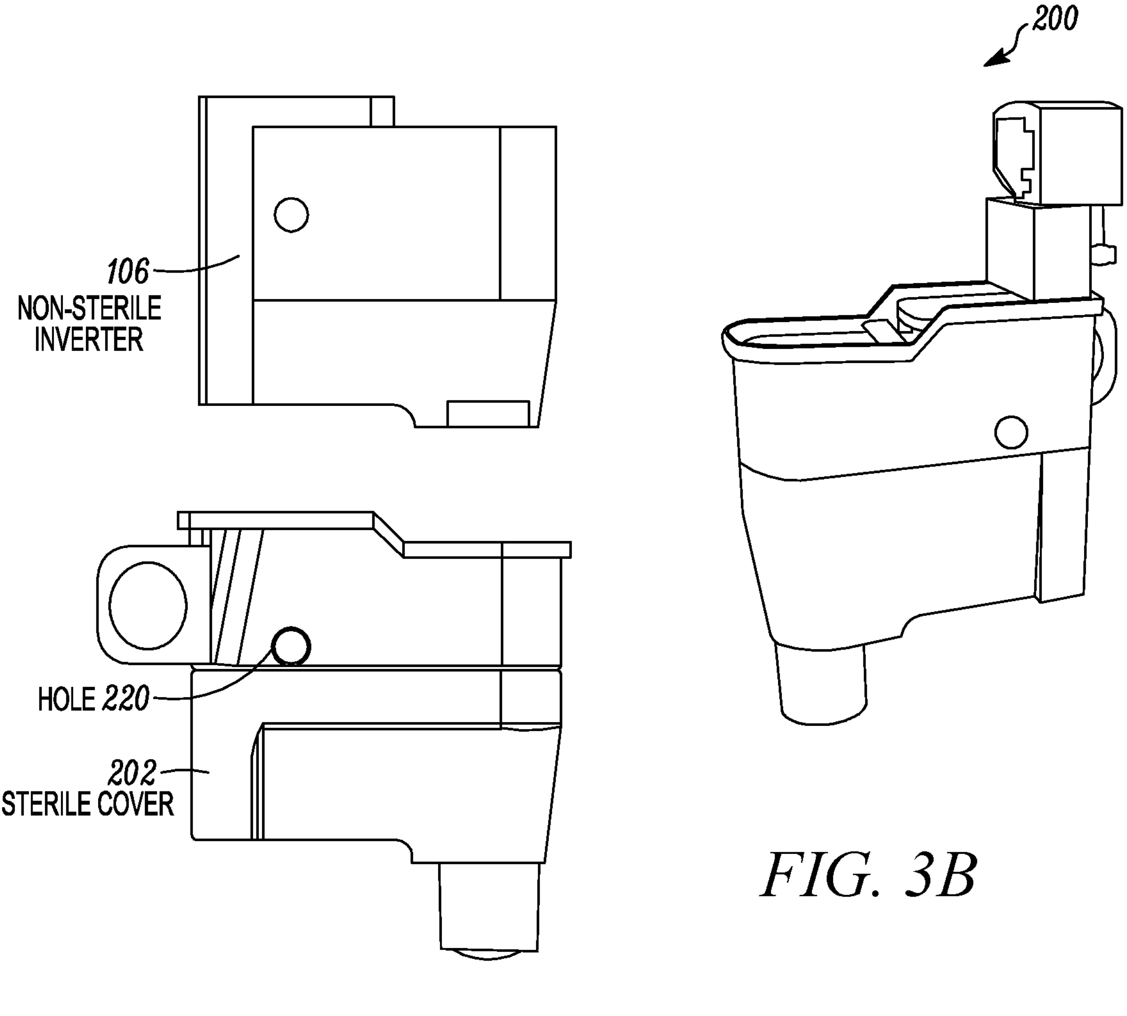
FIG. 3A is a schematic diagram that illustrates an example of a side view of the non-sterile inverter of FIG. 1A and the sterile cover of FIGS. 2A-2C, according to an embodiment.
FIG. 3B is a schematic diagram that illustrates an example of a side view of the non-sterile inverter secured within the sterile cover of FIG. 3A, according to an embodiment.

FIG. 3A is a schematic diagram that illustrates an example of a side view of the non-sterile inverter 106 of FIG. 1A and the sterile cover 202 of FIGS. 2A-2C, according to an embodiment. FIG. 3B is a schematic diagram that illustrates an example of a side view of the non-sterile inverter 106 secured within the sterile cover 202 of FIG. 3A, according to an embodiment. To position the non-sterile inverter 106 into the sterile cover 202, a base of the non-sterile inverter 106 is slid into an opening at a top of the sterile cover 202 and pushed until a lower aperture 404 (FIG. 4B) of the non-sterile inverter 106 engages a tapered lip 203 adjacent a base of the first portion 210 of the sterile cover 202. As also depicted in FIG. 3A, in an embodiment, the sterile cover 202 defines one or more openings 220 to receive knobs 112 of the non-sterile inverter 106. However, in other embodiments, one or more knobs are positioned at the location of the openings 220 and are integral and/or made from the same material as the sterile cover 202. In an example embodiment, as depicted in FIG. 4H, a modified knob 412 is provided that features a snap feature to receive the knob 412 in the opening 220 of the cover 202. In another example embodiment, the modified knob 412 is threadably received in the opening 220 of the cover 202 (e.g. external threads on the knob 412 engage internal threads in the opening 220). In this embodiment, once received, the modified one or more knobs 412 become permanently retained within the sterile cover 202 for purpose of adjusting the inverter 106. This advantageously allows the user to dispose of the sterile cover 202 and the modified one or more knobs 412 as one piece and/or advantageously discourages the reuse/sterilization of the knobs 112.

Figures 4A, 4B:
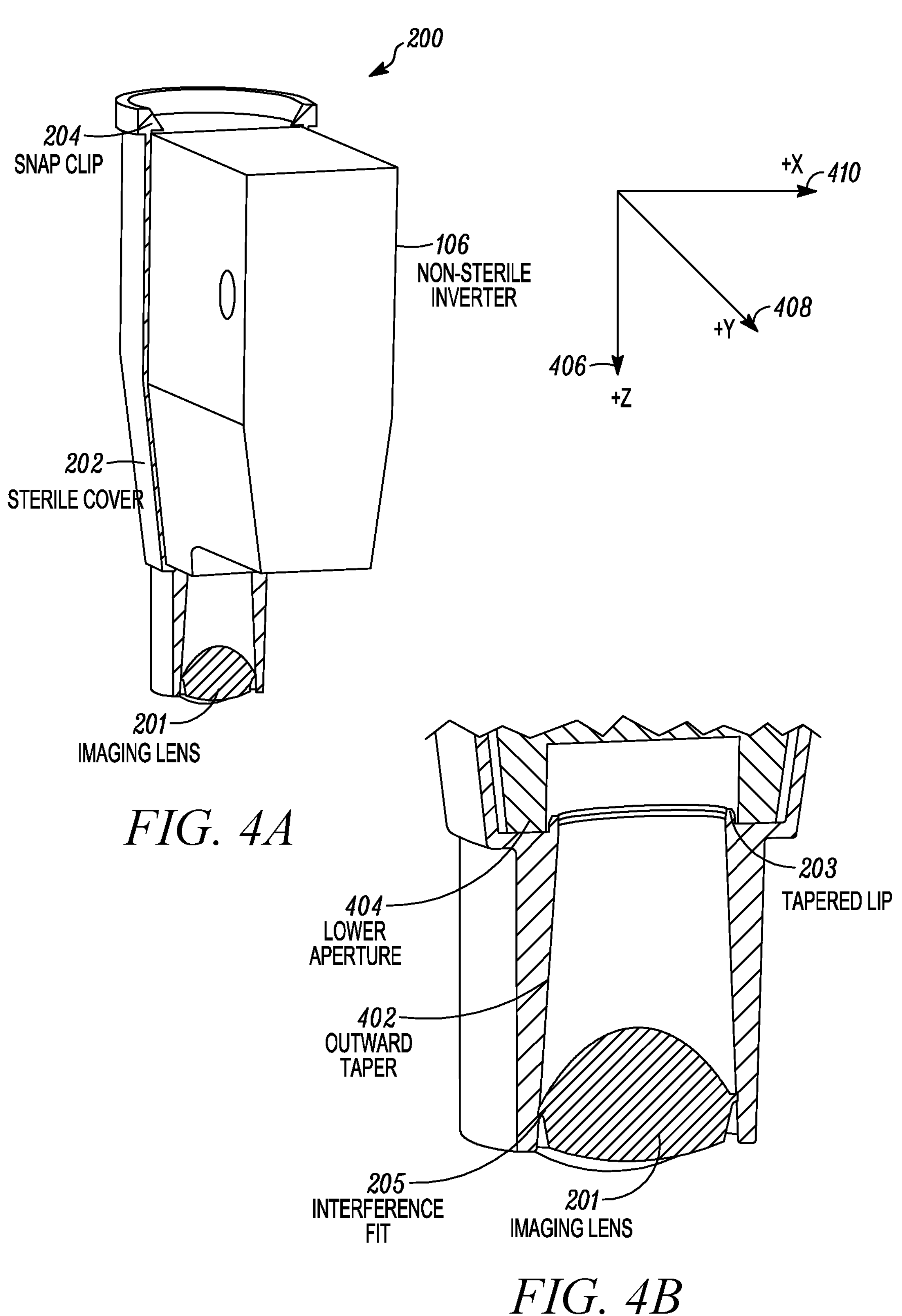
FIGS. 4A-4D are images that illustrate example cross-sectional views of the non-sterile inverter secured within the sterile cover of FIG. 3B, according to an embodiment.

FIGS. 4A-4D are images that illustrate example cross-sectional views of the non-sterile inverter 106 secured within the sterile cover 202 of FIG. 3B, according to an embodiment. In an embodiment, FIG. 4A depicts that the first portion 210 of the sterile cover 202 includes a structural feature, such as a snap clip 204 configured to engage the non-sterile inverter 106 to secure the non-sterile inverter 106 along a first axis 406 (Z axis) defined by an optical axis 407 (FIG. 5A) of the non-sterile inverter 106 and imaging lens 201. The optical axis 407 is defined in the frame of reference of the sterile cover 202. As previously discussed, the non-sterile inverter 106 is positioned within the sterile cover 202 by inserting the base of the non-sterile inverter 106 through an opening in a top of the sterile cover 202. As the top of the non-sterile inverter 106 passes the top of the sterile cover 202, the snap clip 204 deflects outward and then inward to secure over the top of the non-sterile inverter 106. This advantageously secures the non-sterile inverter 106 within the first cavity 211 and specifically prevents movement of the non-sterile inverter 106 along the first axis 406.

In some embodiments a plurality of snap clips 204 are provided (e.g. spaced apart) along a perimeter of the top of the sterile cover (e.g. as shown in FIG. 2C). In other embodiments, structures other than a snap clip can be used at the top of the sterile cover 202 to secure the non-sterile inverter 106 along the first axis 406. FIGS. 4E through 4G depict other embodiments of securement structures 204', 204'', 204''' that can be employed instead of the snap clip 204, in order to secure the non-sterile inverter 106 in the sterile cover 202 along the first axis 406. In some embodiments, the securement structures 204', 204'', 204''' can be of any length, number and/or can be contiguous around the entire perimeter of the sterile cover 202. In an example embodiment, any one of the securement structures depicted in any of FIGS. 4E through 4G can be used around the perimeter (e.g. spaced apart) of the sterile cover 202. In one example embodiment, a combination of different securement structures depicted in any of FIGS. 4E through 4G can be used around the perimeter. The inventors recognized that one advantage including a combination of different securement structures is that it is easier to implement in a molded part in regards to the parting line of the mold.

In another embodiment, as shown in FIG. 4B the first portion 210 of the sterile cover 202 includes a lip 203 configured to engage a lower aperture 404 of the non-sterile inverter 106. In one embodiment, the lip 203 engages the lower aperture 404 to secure the non-sterile inverter 106 along a second axis 408 (Y axis) and a third axis 410 (X axis) which are both orthogonal to the first axis 406 oriented in a direction from the first portion 210 to the second portion 212. In an example embodiment, the lip 203 and the lower aperture 404 are circular and/or oval shaped where an inner diameter of the lower aperture 404 is greater than an outer diameter of the tapered lip 203. In an example embodiment, the inner diameter of the lower aperture 404 is about 18.0 mm or in a range from about 15.0 mm to about 21.0 mm and the outer diameter of the tapered lip 203 is about 17.8 mm or in a range from about 15.2 mm to about 21.2 mm. In some embodiments, the values of the inner diameter of the lower aperture 404 and/or the outer diameter of the tapered lip 203 can differ based on the viewing device (e.g. Haag-Streit has released a few versions of the EIBOS® inverter). In one example embodiment, the values of the inner diameter of the lower aperture 404 and the outer diameter of the tapered lip 203 are based on the EIBOS® 2 inverter and/or any future releases from Haag-Streit. In one embodiment, the lip 203 is a tapered lip, e.g. a taper which was designed such that the top of the lip 203 has sufficient clearance between the outer diameter of the tapered lip 203 and the inner diameter of the lower aperture 404. In an example embodiment, as the non-sterile inverter 106 gets lowered into the sterile cover 202, this clearance as a result of the taper restricts the movement to a maximum (e.g. about 0.1 mm) in each direction (e.g. 17.8 mm outer diameter of the lip 203 and 18.0 mm inner diameter of the lower aperture 404). In another embodiment, an outward taper 402 is defined in the second portion 212 of the sterile cover 202 for moldability. In still other embodiments, the lip 203 is non-tapered.

In another embodiment, as depicted in FIG. 4B, the second portion 212 of the sterile cover 202 includes an interference fit 205 configured to engage the imaging lens 201 to secure the imaging lens 201 along the first axis 406, the second axis 408 and the third axis 410. In an example embodiment, the imaging lens 201 is one or more of a wide angle imaging lens used for a microscope, such as an ophthalmic operating microscope. In an example embodiment, the imaging lens 201 is a single lens, or system of multiple lenses. In an example embodiment, the imaging lens 201 has a combined diopter number of about 50 to 130 diopters designed to image the retina onto a virtual image plane situated above the upper apex of the imaging lens. In an example embodiment, the imaging lens 201 is a single bi-convex lens with aspheric surfaces, injection molded out of Polymethyl methacrylate (PMMA). In still other example embodiments, the imaging lens 201 is made from other lens materials such as optically clear plastics or ceramics. In an example embodiment, the plastics might include one or more of Polycarbonate, Polystyrene, or co-polymers, while ceramics might include one or more of glass, silica, or quartz. In still other example embodiments, the imaging lens 201 is formed using one or more manufacturing methods such as Computer Numerical Control (CNC) machining (single point diamond turning), pressing, grinding, 3D printing and other additive manufacturing techniques In an example embodiment, the interference fit 205 is achieved based on the lens 201 having an outer diameter of about 18 mm or in a range from about 15 mm to about 21 mm and secured along the outward taper 402 where the inner diameter of the sterile cover 202 is about 0.1-0.3 mm smaller than the outer diameter of the lens 201. In one embodiment, the interference fit 205 includes a groove at a specific location on the interior wall of the second portion 212 and the outer diameter of the lens is sized to fall into the groove. In one embodiment, the groove is located so that the lens is positioned a certain distance (e.g. about 16.3 mm or in a range from about 8 mm to about 18 mm) away from the lower face of the inverters lower aperature 404. In yet another embodiment, the optimal position is the position to allow for the range of focusing necessary to view all sections of the ocular fundus (e.g. in a range from about 0 mm to about 30 mm, depending on the imaging lens 201).

Figure 4C:
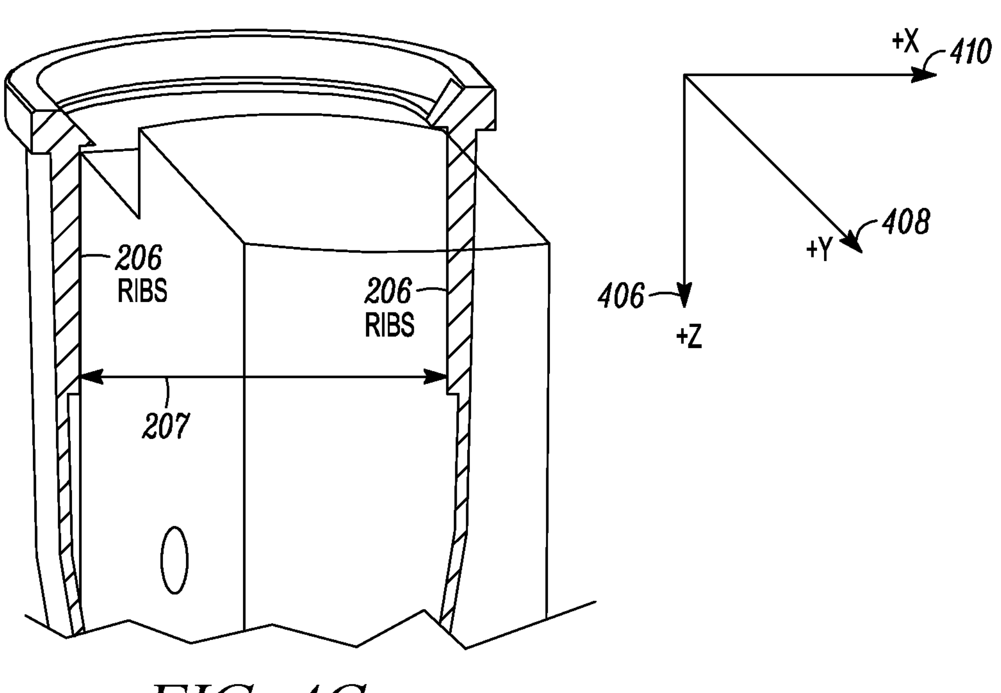
Figure 4D:
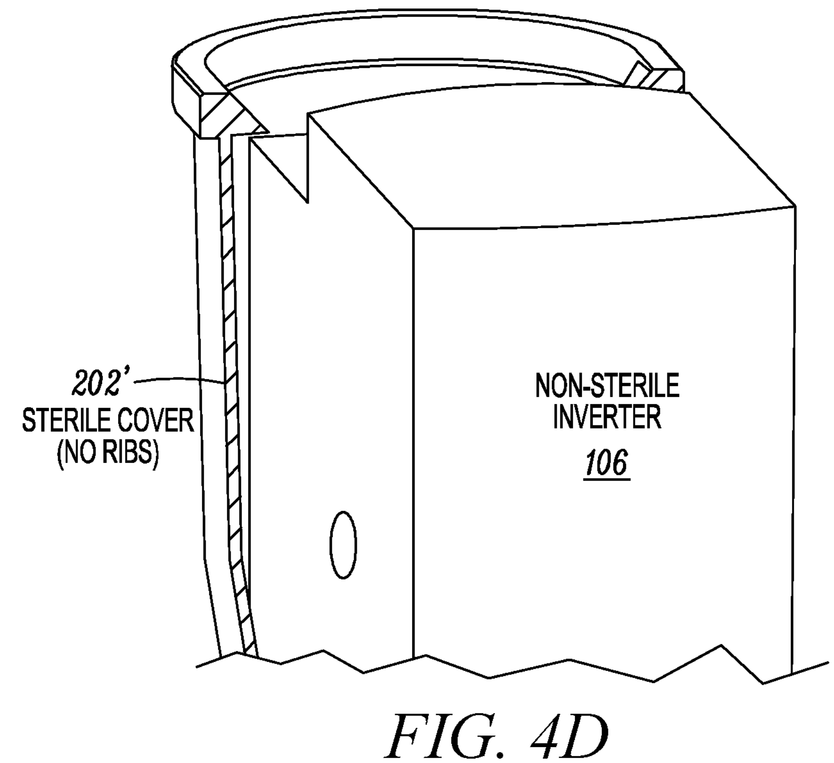
Figures 4E, 4F, 4G:
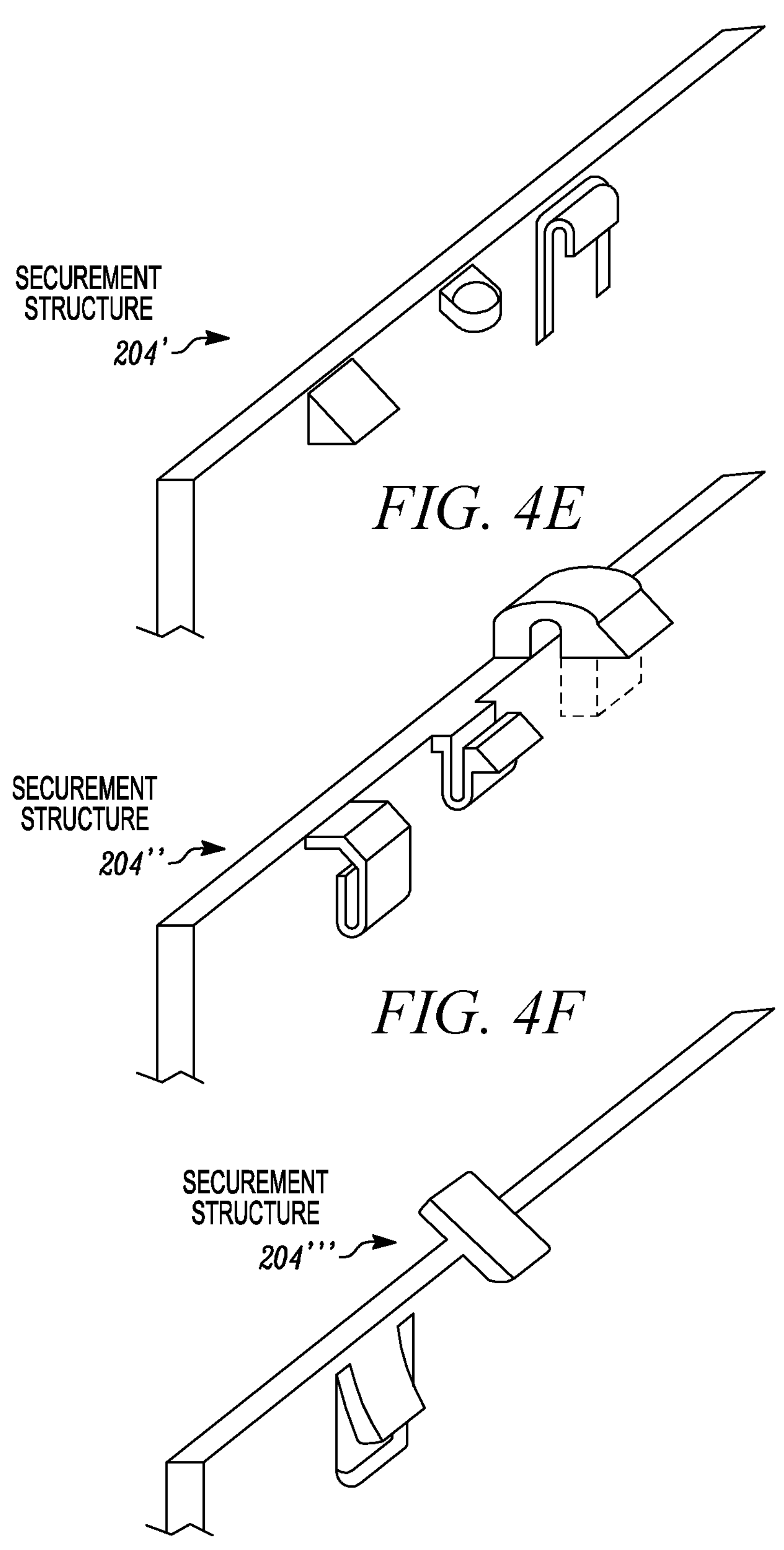
FIGS. 4E-4G are images that illustrate example side perspective views of securement structures along a top of the sterile cover of FIG. 3B, according to various embodiments.
Figure 4H:
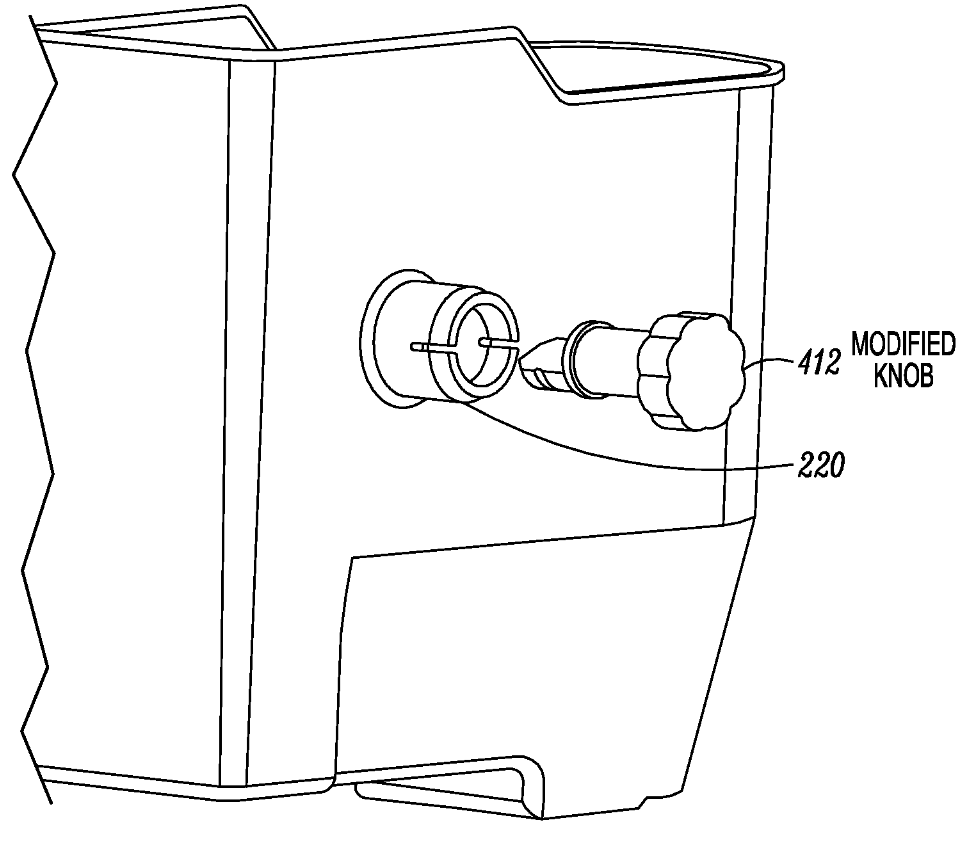
FIG. 4H is a schematic diagram that illustrates an example of a side perspective view of a click-in knob into the sterile cover of FIGS. 2A-2C, according to an embodiment.

In another embodiment, as depicted in FIG. 4C, the first portion 210 of the sterile cover 202 includes a pair of ribs 206 spaced apart along the second axis 410 orthogonal to the first axis 406 and the ribs 206 placed parallel to the plane formed by the first axis 406 and second axis 410. In an embodiment, the ribs 206 have a length that is extruded vertically along the first axis 406 and spaced on opposite sides of the non-sterile inverter 106. In an embodiment, the pair of ribs 206 are configured to engage the non-sterile inverter 106 to secure the non-sterile inverter 106 within the first cavity 211 along the second axis 410. In an example embodiment, a thickness of each rib 206 is sized to have a thickness along the second axis 410 so that an inner distance 207 (FIG. 4C) of the first portion 210 between pair of ribs 206 is based on an outer distance of the non-sterile inverter 106 along the second axis 410. In an example embodiment, the thickness of each rib 206 is sized so that the inner distance 207 of the first portion 210 between the pair of ribs 206 is about equal (e.g. within ±10%) of the outer distance of the non-sterile inverter 106 along the second axis 410. This arrangement can be contrasted with FIG. 4D where a sterile cover 202' is shown without the ribs 206 and thus the non-sterile inverter 106 is free to shift along the second axis 410. In some embodiments only one pair of ribs 206 are provided in the sterile cover 202. In other embodiments, a plurality of pairs of ribs 206 are provided (e.g. spaced apart) along the sterile cover 202 (e.g. FIG. 2A showing spaced apart ribs 206 along the first portion 210). In other embodiments, other structures other than ribs can be used in the first portion 210 to secure the non-sterile inverter 106 along the second axis 408. In some embodiments, structures other than ribs 206 could be employed along the first portion 210 such as blisters/bumps, step feature, contiguous circumferential smooth lip, and/or secondary attachments (e.g. slide-in pieces, tape/rubber placed on interior wall).

The various structural features of the sterile cover 202 advantageously secure the non-sterile inverter 106 and imaging lens 201 in one or more directions (e.g. snap clip 204 secures the non-sterile inverter 106 along the first axis 406; tapered lip 203 secures the non-sterile inverter 106 along the second axis 408 and third axis 410; ribs 206 secure the non-sterile inverter 106 along the second axis 408 and interference fit 205 secures the lens 201 along the axes 406, 408, 410). This advantageously ensures that concentricity (e.g. optical axis 407 in FIG. 5A) and correct focus position between the imaging lens 201 and non-sterile inverter 106 is achieved (e.g. the non-sterile inverter 106 and lens 201 are centered along the second axis 410 and third axis 408 and spaced apart along the axis 406 based on the focal length of the lens 201). This is advantageously achieved upon securing the non-sterile inverter 106 within the sterile cover 202 and engaging the lower aperture 404 at the tapered lip 203.

Figures 5A, 5B, 5C:
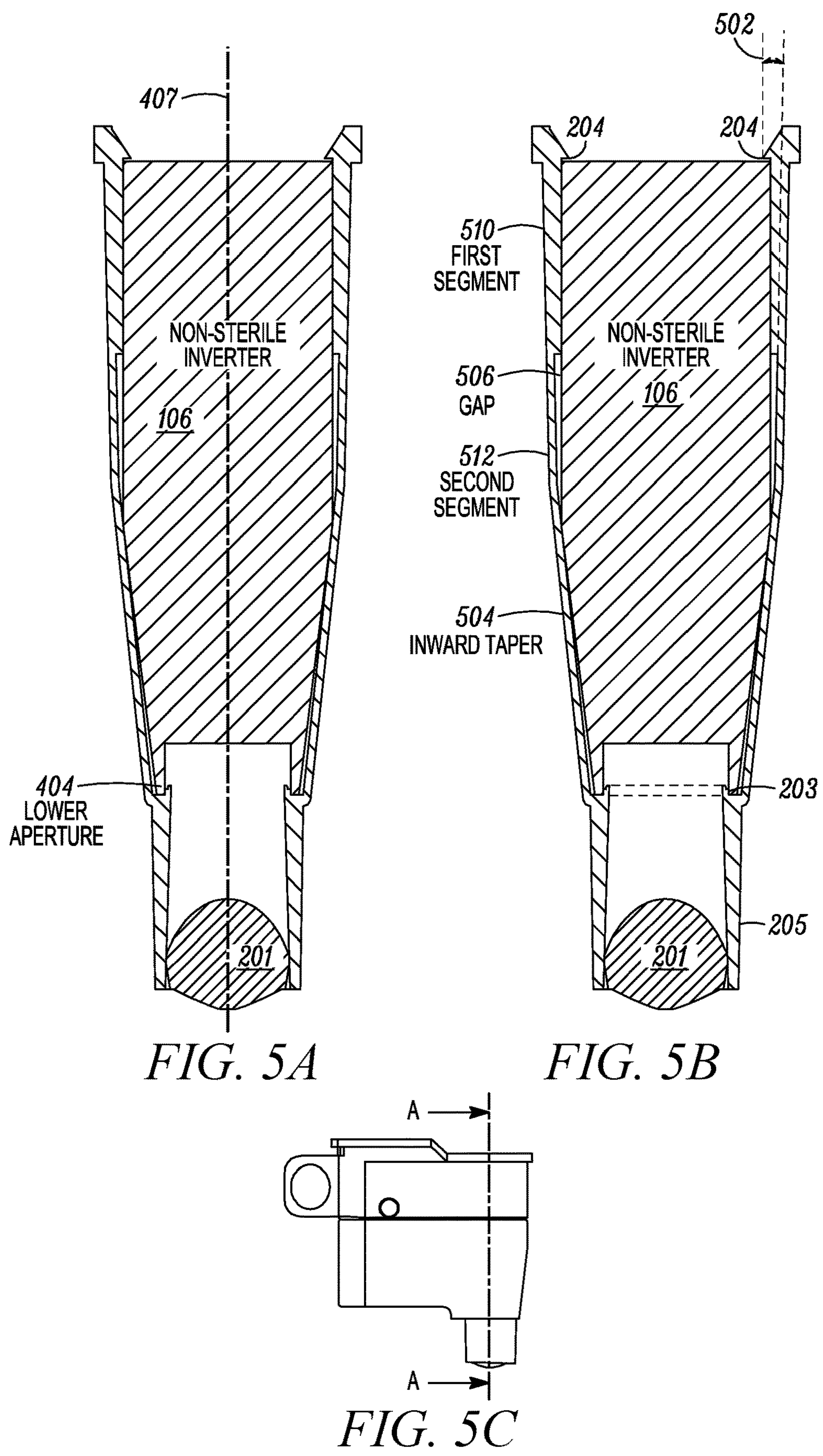
FIGS. 5A-5B are images that illustrate example cross-sectional views of the non-sterile inverter secured within the sterile cover along the line A-A in FIG. 5C, according to an embodiment.
FIG. 5C is a schematic diagram that illustrates an example side view of a sterile cover, according to an embodiment.

FIGS. 5A-5B are images that illustrate example cross-sectional views of the non-sterile inverter 106 secured within the sterile cover 202 along the line A-A in FIG. 5C, according to an embodiment. FIG. 5C is a schematic diagram that illustrates an example side view of a sterile cover 202, according to an embodiment. In an embodiment, FIG. 5B depicts that the first portion 210 defines an inward taper 504 from an intermediate portion to the lip 203. In an example embodiment, the inward taper 504 has a convergence angle of about 8 degrees (or in a range from about 4 degrees to about 12 degrees) and/or is defined based on an inner distance of the first cavity 211 being reduced from about 30.4 mm (or in a range from about 24 mm to about 36 mm) to about 22.0 mm (or in a range from about 18 mm to about 26 mm) adjacent to the lip 203. In another embodiment, the first portion 210 of the sterile cover 202 defines a gap 506 by a termination of the rib 206, where the gap 506 is a consequence of molding a part. In an example embodiment, the height at which the rib 206 ends is a design feature that defines the gap 506 and the mechanism to prevent reuse of the sterile cover 202 discussed below. The gap 506 is provided so that the thickness of the sterile cover 202 is smaller adjacent to the gap 506 than the thickness of the rib 206. This advantageously facilitates the placement and use of the mechanism to prevent reuse of the sterile cover (e.g. permanently break the sterile cover 202 adjacent to the gap 506, since it is easier to break the sterile cover 202 at the reduced thickness region adjacent to the gap 506).

Figures 6A, 6B:
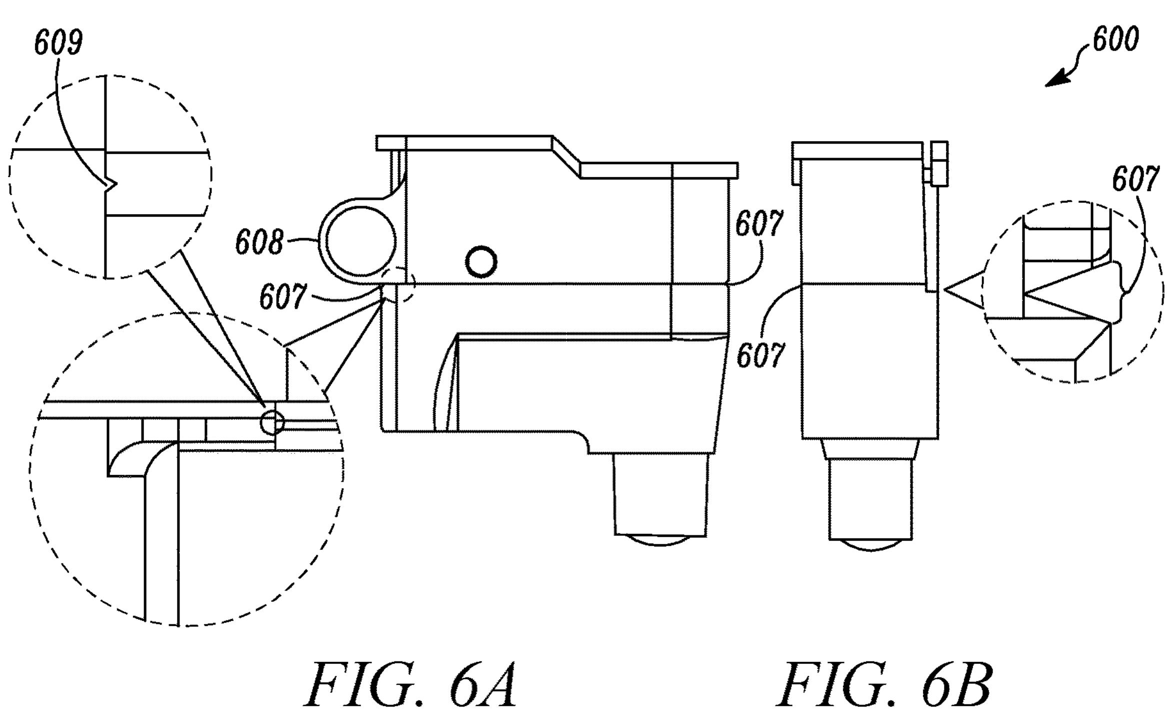
FIGS. 6A-6B are schematic diagrams that illustrate example views of a sterile cover with a tab, according to an embodiment.

FIGS. 6A-6B are schematic diagrams that illustrate example views of a sterile cover 600 with a tab 608, according to an embodiment. In an embodiment, the tab 608 is provided along the first portion 210 of the sterile cover 600. In one embodiment, the tab 608 is provided to disengage the first portion 210 from the non-sterile inverter 106 and/or prevent reuse of the sterile cover 600. In one embodiment, the first portion 210 includes the snap feature 204 configured to engage the non-sterile inverter 106 to secure the non-sterile inverter 106 along the first axis 406. In an embodiment, the tab 608 is provided to permanently disengage the snap feature 204 from the non-sterile inverter 106 to facilitate removal of the non-sterile inverter 106 from the sterile cover 600 along the first axis 406. In an embodiment, the rib 206 is provided along a first segment 510 (FIG. 5B) of the first portion 210. In an example embodiment, a first thickness of the first segment 510 (e.g. about 1 mm plus a thickness of the rib 206) varies from a larger thickness (e.g. about 2.2 mm) adjacent a top of the rib 206 to a smaller thickness (e.g. about 1.5 mm) adjacent a bottom of the rib 206. In one embodiment, the tapered first thickness of the first segment 510 is due to the tapered thickness of the rib 206 from a top of the rib 206 to a bottom of the rib 206. In an embodiment, the tab 608 is provided along a second segment 512 (e.g. adjacent the gap 506 of FIG. 5B) of the first portion 210 of the sterile cover 600 with a second thickness (e.g. about 1 mm) that is less than the first thickness (e.g. about 1 mm plus the thickness of the rib 206) of the first segment 510.

In one example embodiment, the second thickness varies from a larger thickness (e.g. about 1 mm) to a smaller thickness (e.g. about 0.3 mm) adjacent a pre-scored line 607. In yet another embodiment, the second segment 512 of the first portion 210 of the sterile cover 600 includes the pre-scored line 607 that projects into the first portion 210 parallel to a plane defined by the second axis 410 and third axis 408. In an example embodiment, the pre-scored line 607 leaves a material thickness of about 0.3 mm or in a range from about 0.1 mm to about 0.5 mm. In an embodiment the pre-scored line 607 extends an entire length of the side of the sterile cover 600. In still other embodiments, the pre-scored line 607 extends only a portion of the length of the side of the sterile cover 600 and/or around the entire sterile cover 600. Additionally, in yet another embodiment, the second segment 512 of the first portion 210 includes a notch 609 oriented in a direction orthogonal to the pre-scored line 607 (e.g. third axis 410). In an example embodiment, the notch 609 has a depth in a range from about 0 mm to about 10 mm. The pre-scored line 607 and/or notch 609 advantageously make it easier to sever and/or break the first portion 210 with the tab 608. In some embodiments, the pre-scored line 607 can vary in depth and can include complete perforation in some areas and variable depth in other areas.

Figures 6C, 6D, 6E:
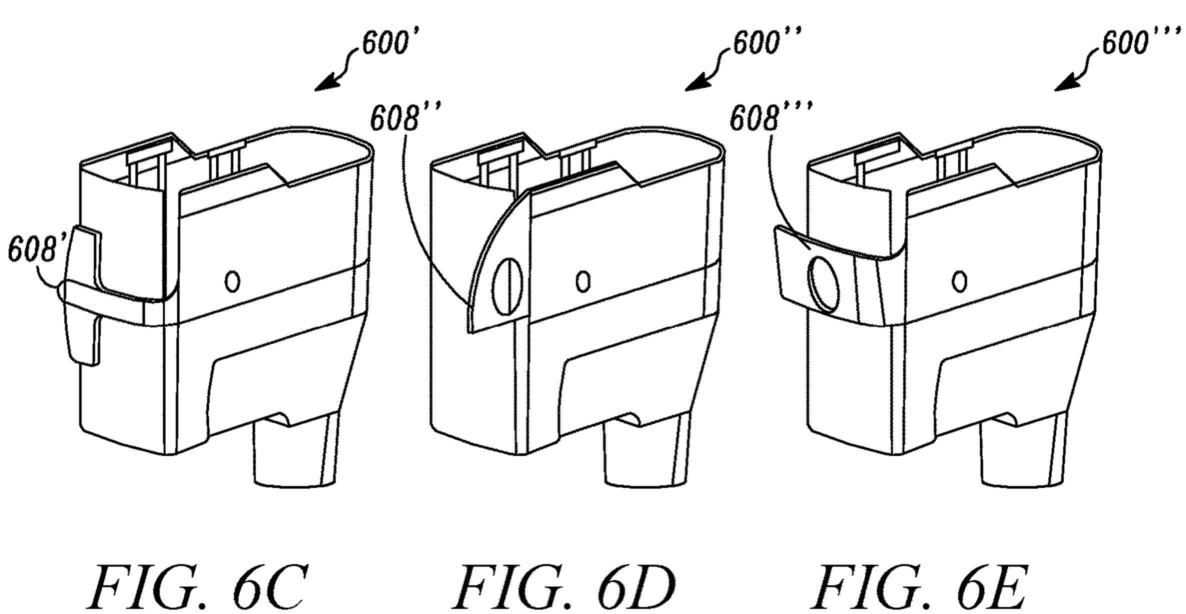
FIGS. 6C-6H are schematic diagrams that illustrate example views of sterile covers with tabs, according to various embodiments.
Figure 6F:
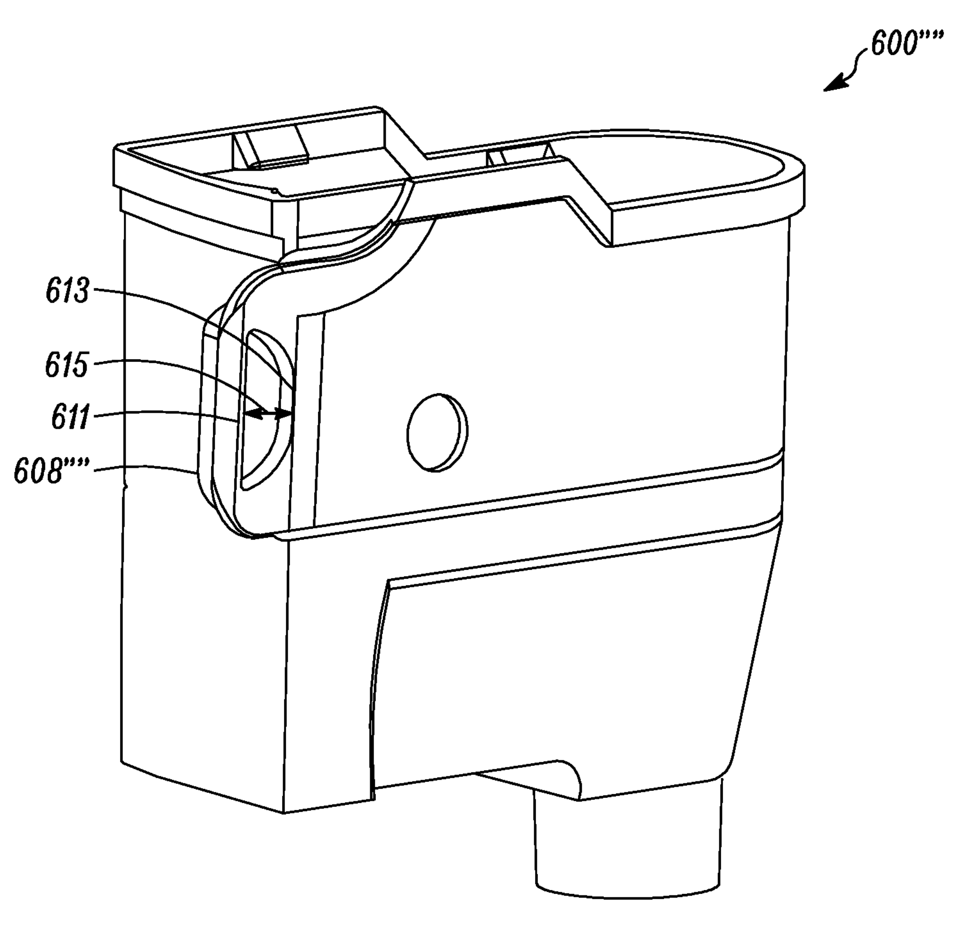
Figure 6G:
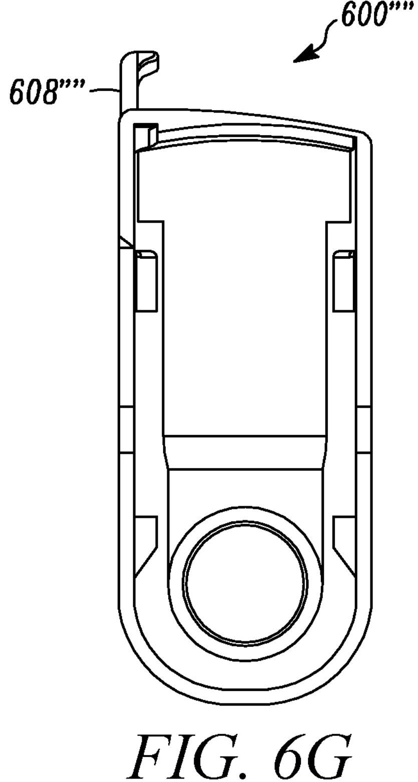
Figure 6H:
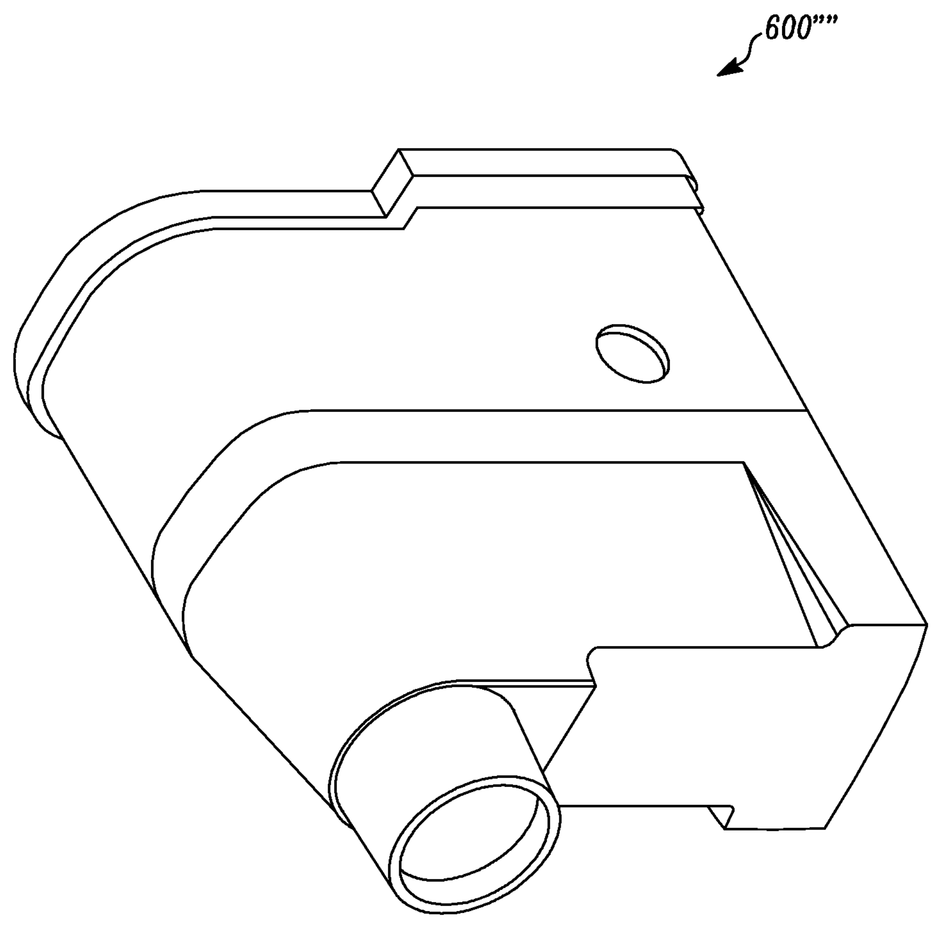

FIGS. 6C-6H are schematic diagrams that illustrate example views of sterile covers 600', 600", 600'", 600"" with a tab, according to various an embodiment. In an embodiment, the tabs of the sterile covers of FIGS. 6C-6H are variations on the tab 608 of FIGS. 6A-6B. In an embodiment, the tabs have one or more similar characteristics (e.g. define an opening that has sufficient dimensions for a user to insert their fingers/hand as shown in FIGS. 6A and 6D-6H or define a handle with sufficient dimensions for a user to grasp the handle with their fingers/hand as shown in FIG. 6C). In one embodiment, the tab 608' of FIG. 6C does not feature an opening to grab the tab but rather features a pair of wings for the user to grab. In another embodiment, the tab 608" of FIG. 6D is an extension of the first portion 210 of the sterile cover 600 and defines an opening which the user can grab. In yet another embodiment, the tab 608'" of FIG. 6E is similar to the tab 608" but is angled relative to the first portion 210 of the sterile cover 600. In yet another embodiment, the tab 608"" of FIGS. 6F through 6H is similar to the tab 608" of FIG. 6D with the exception that an opening of the tab has a different shape than the tab 608" (e.g. arcuate shape around the perimeter of the opening). In one example embodiment, in contrast with the opening defining the tab 608" of FIG. 6D (e.g. circular or oval shape around the perimeter of the opening) the opening defining the tab 608"" of FIGS. 6F through 6H includes a first portion 611 that is flat and a second portion 613 that is arcuate. In another example embodiment, the opening defining the tab 608"" is shaped to be easily grabbed by a hand of a user such that a base surface of the hand (e.g. palm) engages the flat portion of the opening and a top surface of the hand (e.g. adjacent the knuckles) faces the second arcuate portion. In an example embodiment the first portion 611 has a length of about 10 mm or in a range from about 6 mm to about 20 mm and the second portion 613 is separated from the first portion 611 by a distance 615 of about 6 mm. Although tabs are provided in each embodiment of FIGS. 6A-6H, any structure that can be used and physically actuated by a user to separate the snap feature 204 from the non-sterile inverter 106 and/or to prevent reuse of the sterile cover and/or the permanently break the sterile cover can be used in the present invention. In an example embodiment, other possibilities of a separation line include but are not limited to imbedded wire/string and a blade/zipper wedge.

Figure 7:
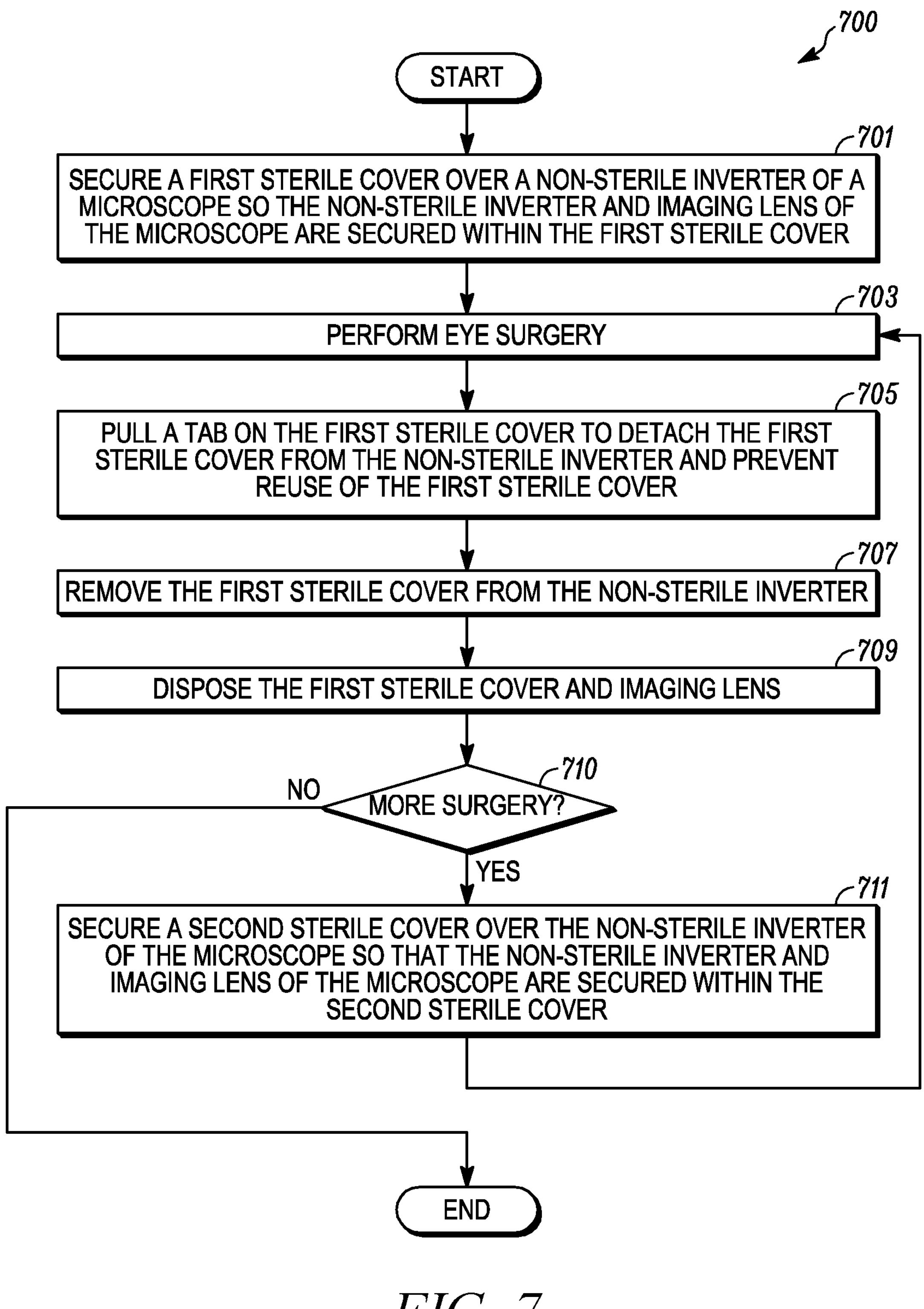
FIG. 7 is a flowchart that illustrates an example of a method for using the sterile cover of FIGS. 2A-2C with a microscope, according to an embodiment.

FIG. 7 is a flowchart that illustrates an example of a method 700 for using the sterile cover 202 of FIGS. 2A-2C with a viewing device such as a microscope, according to an embodiment. In an embodiment, step 701 includes removing a preassembled first sterile cover 202 from a sterile packaging, where the preassembled first sterile cover 202 includes the imaging lens 201 pre-secured (e.g. before step 701) within the second portion 212 of the sterile cover 202. In one embodiment, in step 701 a first sterile cover 202 is secured over the non-sterile inverter 106 of the viewing device so that the non-sterile inverter 106 and imaging lens 201 (e.g. secured within the second portion 212 of the sterile cover 202 before step 701) are secured or positioned within the first sterile cover 202. In an embodiment, in step 701, a base of the non-sterile inverter 106 is inserted within an opening at a top of the sterile cover 202. Since the base of the non-sterile inverter 106 has a smaller dimension than an opening at the top of the sterile cover 202, the base of the non-sterile inverter 106 can be inserted within the top of the sterile cover 202. In this embodiment, in step 701, the non-sterile inverter 106 is continuously moved into the first sterile cover 202 until the lower aperture 404 of the non-sterile inverter 106 engages the tapered lip 203 of the first sterile cover 202 (FIG. 4B) and/or the snap features 204 deflected outward then inward and engage the top of the non-sterile inverter 106 (FIG. 4A). In this embodiment, the first sterile cover 202 already includes the lens 201 secured within the second portion 212 with the interference fit 205. After step 701 is performed, the non-sterile inverter 106 and lens 201 are concentrically positioned and in proper focal position with respect to each other.

In step 703, a medical procedure is performed with the microscope (e.g. eye surgery is performed on a subject). In an embodiment, in step 703, the sterile cover 202 and non-sterile inverter 106 are rotated from a first position (e.g. where the optical axis 407 is aligned with axis 410) to a second position (e.g. where the optical axis 407 is aligned with the axis 406). The microscope is then used to perform eye surgery on the patient. In one embodiment, during various stages of the eye surgery, the sterile cover 202 and non-sterile inverter 106 can be rotated from the first position to the second position, to provide free access to the eye for the surgeon and/or to image anterior anatomy of the eye.

In step 705, the tab 608 is pulled along the first portion 210 of the sterile cover 202. In one embodiment, in step 705, the tab 608 is pulled to detach the first portion 210 and snap clip 204 from the non-sterile inverter 106, to ease the removal of the non-sterile inverter 106 from the sterile cover 202. In another embodiment, in step 705 the tab 608 is pulled to permanently break the first portion 210 (e.g. along the line 607) to prevent reuse of the sterile cover 202.

In step 707, the first sterile cover 202 is removed from the non-sterile inverter 106. In an embodiment, in step 707, after performing step 705 the snap cover 204 has disengaged the top of the non-sterile inverter 106 and thus the first sterile cover 202 can be easily slid off the non-sterile inverter 106. In step 709, the first sterile cover 202 (and lens 201 within the second portion 212) is disposed.

In an embodiment, after step 709 the method proceeds to block 710 where it is determined whether further medial procedures (e.g. surgery) need to be performed with the microscope. In one embodiment, in block 710 it is determined whether additional surgery needs to be performed (e.g. with additional patients). In still another embodiment, in block 710 it is determined whether a newly sterilized field is required. If the determination in block 710 is in the affirmative, the method proceeds to step 711. If the determination in block 710 is in the negative, the method ends.

In one embodiment, in step 711 for a newly sterilized field (e.g. new patient requiring a newly sterilized field), a second sterile cover 202 is positioned over the non-sterile inverter 106 in a similar manner as the first sterile cover 202 was positioned over the non-sterile inverter 106 in step 701. This advantageously involves only one step to prepare the microscope for the next eye surgery instead of the numerous sterilization and disassembly steps involved in the conventional microscope systems and covers. In an embodiment, the method then restarts with step 711 for each additional procedure where it is determined in block 710 that a newly sterilized field is required. If this determination in block 710 is affirmative, the method continues from step 711 back to steps 703, 705, 707, 709 and block 710, which are repeated with new sterile cover. If this determination in block 710 is negative, the method ends.

Figure 8:
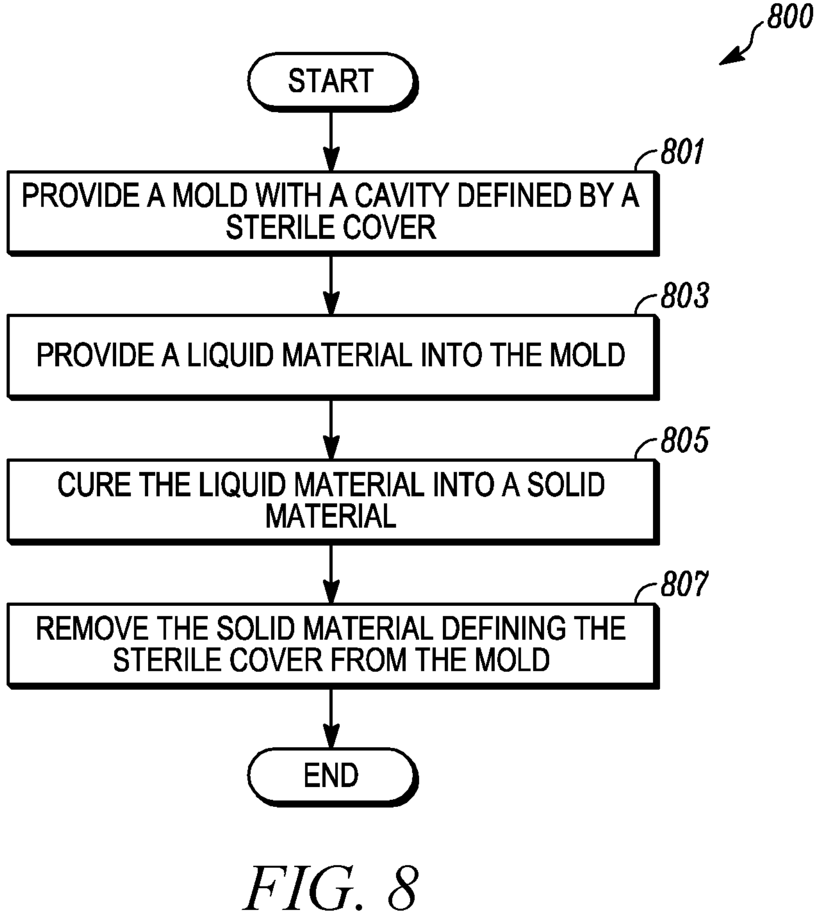
FIG. 8 is a flowchart that illustrates an example of a casting method for forming the sterile cover of FIGS. 2A-2C, according to an embodiment.

FIG. 8 is a flowchart that illustrates an example of a molding method 800 for forming the sterile cover 202 of FIGS. 2A-2C, according to an embodiment. In step 801, a mold is provided with a cavity defined by the sterile cover 202. In an embodiment, the mold includes core elements based on gaps in the sterile cover 202, such as the gap 506 (FIG. 5B). In another embodiment, the cavity of the mold includes angles to form the sterile cover 202 including a draft angle 502 (FIG. 5B) which is used to define the width of the ribs 206. In an example embodiment, the draft angle 502 is about 2 degrees or in a range from about 0.25 degrees to about 3 degrees.

In step 803, a liquid material is provided into the mold. In an embodiment, the liquid material is a gamma stable, semi-rigid thermoplastic material. In an embodiment, in step 805, the liquid material is cured into a solid material. In one embodiment, in step 805 the mold is closed which takes a certain time period (e.g. about 1-2 seconds). In another embodiment, in step 805 the liquid material is injected into the mold, over a certain time period (e.g. about 2-5 seconds). In an example embodiment, a mold temperature (e.g. for PP material) is in a range from about 70 degrees Fahrenheit (F) to about 150 degrees F. In another embodiment, a temperature of the liquid material (e.g. PP material) at injection is in a range from about 375 degrees F. to about 450 degrees F.

In step 807, the cured material is removed from the mold and defines the sterile cover 202. In an example embodiment, in step 807 various steps are performed over certain time periods such as pack and hold (e.g. about 8-10 seconds); part cooling (e.g. about 10-30 seconds); screw return (e.g. about 2-5 seconds); mold opening (e.g. about 1 second) and ejection (e.g. about 1 second). In still another embodiment, a step is also performed to assemble the cover and the lens (e.g. securing the lens within the sterile cover with the interference fit) and/or placing the assembled cover in a sterilized packaging. In an embodiment, the sterile cover 202 is then used such as in the method 700. In another embodiment, multiple sterile covers are formed using the method 800 so that multiple sterile covers can be used during the method 700.

Although FIG. 8 depicts a flowchart of one method (e.g. molding) for forming the sterile cover 202, the embodiments of the present invention encompasses any method that can be used to form the sterile cover 202. In one example embodiment, the embodiments of the present invention include a method for forming the sterile cover 202 using additive manufacturing techniques. In this example embodiment, the method includes generating a data file with information indicating the shape and/or contours of the sterile cover 202. In this example embodiment, the data file is then used by the additive manufacturing machine to produce the sterile cover 202. In an embodiment, a 3D-printer (e.g. stereolithography 3D printer) may be used to produce the sterile cover 202, in stacked two-dimensional layers. In one example embodiment, the sterile cover 202 is produced in the stacked two-dimensional layers using an optical beam (e.g. laser, such as a CNC controlled ultraviolet laser) to cure a photopolymer resin into a solid plastic with one of more characteristics of the sterile cover 202 discussed herein (e.g. material properties, dimensions, etc.).

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word “comprise” and its variations, such as “comprises” and “comprising,” will be understood to imply the inclusion of a stated item, element or step or group of items, elements or steps but not the exclusion of any other item, element or step or group of items, elements or steps. Furthermore, the indefinite article “a” or “an” is meant to indicate one or more of the item, element or step modified by the article.

What is claimed is:

1. An apparatus comprising:

a sterile cover including;

a first portion that defines a first cavity such that the first portion is configured to secure a non-sterile inverter of a wide angle viewing attachment for a microscope within the first cavity, and a second portion integral with the first portion, said second portion defines a second cavity continuous with the first cavity, said second portion configured to secure an imaging lens of the wide angle viewing attachment for the microscope within the second cavity; and a tab provided to permanently disengage the sterile cover from the non-sterile inverter and destructively break the sterile cover to prevent reuse of the sterile cover.

2. The apparatus of claim 1, wherein the first portion and the second portion of the sterile cover are made from the same material and wherein the same material is a semi-rigid material.

3. The apparatus of claim 2, wherein the semi-rigid material of the first and second portion has a flexural modulus of greater than 100 MPa.

4. The apparatus of claim 1, wherein the sterile cover is made from a sterilizable material.

5. The apparatus of claim 1, further comprising the imaging lens secured within the second cavity, wherein the imaging lens is disposable.

6. The apparatus of claim 5, wherein the sterile cover defines a first opening in the first portion configured to receive a base of the non-sterile inverter and a second opening in the second portion and wherein the imaging lens is secured within the second opening and wherein the imaging lens is made from a sterilizable material.

7. The apparatus of claim 1, wherein the first cavity has a larger volume than the second cavity.

8. The apparatus of claim 1, wherein the imaging lens is a sterile imaging lens and wherein the first portion and second portion are configured to secure the non-sterile inverter and the sterile imaging lens along a common optical axis oriented in a direction from the first portion to the second portion.

9. The apparatus of claim 1, wherein the imaging lens is a sterile imaging lens and wherein the first portion includes at least one snap feature configured to engage the non-sterile inverter to secure the non-sterile inverter along a first axis defined by an optical axis of the non-sterile inverter and the sterile imaging lens.

10. The apparatus of claim 9, wherein the at least one snap feature includes a plurality of snap features spaced apart along a perimeter of a top of the first portion and wherein each snap feature is configured to engage the non-sterile inverter or its associated fixturing to resist movement of the non-sterile inverter along the first axis.

11. The apparatus of claim 1, wherein the first portion includes at least one pair of ribs spaced apart along a second axis orthogonal to a first axis oriented in a direction from the first portion to the second portion, said at least one pair of ribs configured to engage the non-sterile inverter to secure the non-sterile inverter along the second axis.

12. The apparatus of claim 11, wherein a thickness of each rib in the pair of ribs are is sized to have a thickness along the second axis so that an inner distance of the first portion between pair of ribs is based on an outer distance of the non-sterile inverter along the second axis engaged by the pair of ribs.

13. The apparatus of claim 1, wherein the first portion includes a lip configured to engage a lower aperture of the non-sterile inverter to secure the non-sterile inverter along a second axis and a third axis, wherein the second axis and the third axis are orthogonal to a first axis oriented in a direction from the first portion to the second portion.

14. The apparatus of claim 1, wherein the second portion includes an interference fit configured to engage the imaging lens to secure the imaging lens along a first axis, a second axis and a third axis, wherein the second axis and the third axis are orthogonal to the first axis and wherein the first axis is oriented in a direction from the first portion to the second portion.

15. The apparatus of claim 1, wherein the tab is provided along the first portion of the sterile cover to destructively break the first portion to prevent reuse of the sterile cover and wherein the tab defines at least one of:

an opening with dimensions to receive a portion of the fingers or hand of a user;

a handle with dimensions for a user to grasp the handle; and a pair of wings with dimensions for a user to gras the pair of wings.

16. The apparatus of claim 1, wherein the tab is provided along the first portion of the sterile cover to destructively break the first portion to prevent reuse of the sterile cover and wherein the first portion includes at least one snap feature configured to engage the non-sterile inverter to secure the non-sterile inverter along a first axis defined by an optical axis of the non-sterile inverter and imaging lens and wherein the tab is provided to permanently disengage the at least one snap feature from the non-sterile inverter to facilitate removal of the non-sterile inverter from the sterile cover along the first axis.

17. The apparatus of claim 1, wherein the tab is provided along the first portion of the sterile cover to destructively break the first portion to prevent reuse of the sterile cover and wherein the tab is provided along a second segment of the first portion having a second thickness and wherein a first segment of the first portion adjacent to the second segment has a first thickness that is greater than the second thickness.

18. The apparatus of claim 17, wherein the second segment of the first portion comprises a pre-scored line that projects into the first portion.

19. The apparatus of claim 17, wherein the second segment of the first portion comprises a notch oriented in a direction orthogonal to the pre-scored line.

20. A method for forming the sterile cover of the apparatus of claim 1.

21. The method of claim 20, comprising:

providing a mold with a cavity defined by the sterile cover;

providing a liquid material into the mold;

curing the liquid material into a solid material; and
removing the solid material defining the sterile cover from the mold.

22. The method of claim 20, wherein the sterile cover is formed by additive manufacturing.

23. A method for using the microscope including the apparatus of claim 1, comprising:

securing a first sterile cover over the non-sterile inverter of the microscope such that the non-sterile inverter is secured in the first portion of the first sterile cover and the imaging lens is in the second portion of the first sterile cover such that the non-sterile inverter and imaging lens are aligned along an optical axis;

performing eye surgery using the non-sterile inverter and the imaging lens within the first sterile cover;

permanently disengaging, with the tab, the first sterile cover from the non-sterile cover to destructively break the first sterile cover and prevent reuse of the first sterile cover;

removing the first sterile cover from the non-sterile inverter of the microscope;

disposing the first sterile cover and the imaging lens secured in the second portion of the first sterile cover; and securing a second sterile cover over the non-sterile inverter of the microscope such that the non-sterile inverter is secured in the first portion of the second sterile cover and the imaging lens is secured in the second portion of the second sterile cover such that the non-sterile inverter and imaging lens are aligned along an optical axis.

24. The method of claim 23, further comprising rotating the first sterile cover and non-sterile inverter from a first angle to a second angle different from the first angle between the performing and removing step and further comprising rotating the second sterile cover and non-sterile inverter from the second angle to the first angle after the securing the second sterile cover step.

25. The method of claim 23, wherein the permanently disengaging step comprises applying force along the first portion of the first sterile cover to separate the first portion from the non-sterile inverter prior to the removing step.

* * * * *